(12) United States Patent
Hosemann et al.

(10) Patent No.: US 9,555,200 B2
(45) Date of Patent: Jan. 31, 2017

(54) INHALER

(75) Inventors: Michael Hosemann, Cambridge (GB); Desmond Phillips, Cambridge (GB); David Ramble, Cambridge (GB); Sean Reynolds, West Sussex (GB); Edward Vernon-Harcourt, West Sussex (GB)

(73) Assignee: Novartis AG, Basel (CH)

( * ) Notice: Subject to any disclaimer, the term of this patent is extended or adjusted under 35 U.S.C. 154(b) by 495 days.

(21) Appl. No.: 14/005,015

(22) PCT Filed: Mar. 13, 2012

(86) PCT No.: PCT/EP2012/054371
§ 371 (c)(1),
(2), (4) Date: Sep. 13, 2013

(87) PCT Pub. No.: WO2012/123448
PCT Pub. Date: Sep. 20, 2012

(65) Prior Publication Data
US 2014/0000603 A1    Jan. 2, 2014

Related U.S. Application Data

(60) Provisional application No. 61/452,763, filed on Mar. 15, 2011.

(51) Int. Cl.
*A61M 15/00*    (2006.01)

(52) U.S. Cl.
CPC ..... *A61M 15/0028* (2013.01); *A61M 15/0035* (2014.02); *A61M 15/0041* (2014.02);
(Continued)

(58) Field of Classification Search
CPC ................... A61M 2205/52; A61M 2205/336; A61M 220/332; A61M 1/0065; A61M 2205/14; A61M 15/0035; A61M 15/0065; A61M 15/0033; A61M 15/0038; A61M 15/003
See application file for complete search history.

(56) References Cited

U.S. PATENT DOCUMENTS

| 5,331,953 A | 7/1994 | Andersson et al. |
| 5,809,997 A | 9/1998 | Wolf |

(Continued)

FOREIGN PATENT DOCUMENTS

| CA | 2771443 A1 | 2/2012 |
| EP | 1898977 B1 | 4/2010 |

(Continued)

OTHER PUBLICATIONS

International Search Report, PCT/EP2012/054371 (Jun. 15, 2012).

*Primary Examiner* — Bradley Philips
*Assistant Examiner* — Victoria Leszczak
(74) *Attorney, Agent, or Firm* — Michael Mazza

(57) ABSTRACT

The invention relates to an inhaler (1) comprising a capsule housing (2) for containing a medicament capsule (4). The inhaler includes an airflow path (6) through which air flows during an airflow event from at least one air inlet (8) to an outlet (10), the airflow path passing through the capsule housing. There is a first sensor (16), a processor (18) and a power source (20) for powering the processor. The capsule housing is defined by at least one wall (22) and configured such that when a capsule is located in the capsule housing and sufficient air flows along the airflow path through the capsule housing, the capsule moves within the capsule housing. The first sensor is arranged on the inhaler so that it is able to detect the movement of the capsule within the capsule housing and generate a first signal indicative of said movement. The processor receives the first signal from the first sensor and uses said first signal to determine whether the first signal is indicative of the presence, or absence, of a (Continued)

Figure 6:
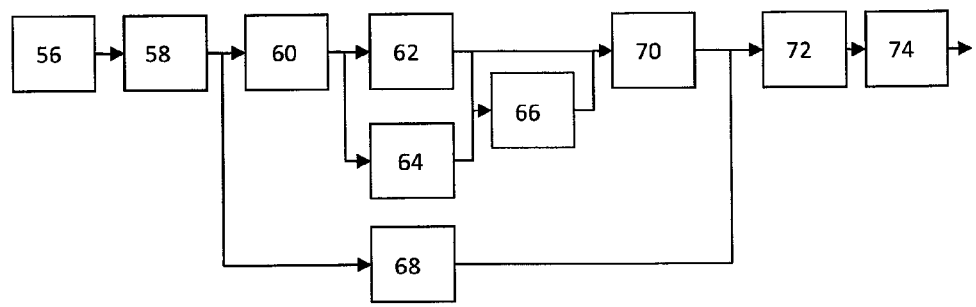

capsule in the capsule housing during an airflow event and generate a capsule signal indicative thereof.

10 Claims, 4 Drawing Sheets

(52) U.S. Cl.
CPC ... *A61M 2202/064* (2013.01); *A61M 2205/14* (2013.01); *A61M 2205/332* (2013.01); *A61M 2205/3306* (2013.01); *A61M 2205/3375* (2013.01); *A61M 2205/3523* (2013.01); *A61M 2205/52* (2013.01); *A61M 2205/8206* (2013.01); *F04C 2270/041* (2013.01)

(56) References Cited

U.S. PATENT DOCUMENTS

| | | | |
|---|---|---|---|
| 5,842,468 A * | 12/1998 | Denyer | A61M 15/0086 128/200.14 |
| 6,116,233 A | 9/2000 | Denyer et al. | |
| 6,119,684 A | 9/2000 | Nohl et al. | |
| 8,474,452 B2 | 7/2013 | Gumaste et al. | |
| 2002/0062829 A1 * | 5/2002 | Ohki | A61M 15/0028 128/203.15 |
| 2005/0022813 A1 | 2/2005 | Alston | |
| 2005/0066735 A1 | 3/2005 | Beavis et al. | |
| 2007/0076067 A1 | 4/2007 | Hamano et al. | |
| 2007/0113843 A1 | 5/2007 | Hughes | |
| 2009/0308397 A1 | 12/2009 | Neame | |

FOREIGN PATENT DOCUMENTS

| | | | |
|---|---|---|---|
| GB | 1596565 A | 1/1978 | |
| GB | 2398065 A | 8/2004 | |
| JP | 2006153760 A | 6/2006 | |
| WO | WO 9507724 A1 * | 3/1995 | ........ A61M 15/0045 |
| WO | 2006053059 A2 | 5/2006 | |
| WO | 2007101438 A1 | 9/2007 | |
| WO | 2007121097 A2 | 10/2007 | |
| WO | 2009075794 A1 | 6/2009 | |

\* cited by examiner

INHALER

The present invention relates to an inhaler, specifically a capsule based inhaler.

There are many types of inhaler known through which a user can inhale to receive a medicament contained therein. Some inhalers contain multiple doses of medicament which can be sequentially accessed by a user, while others are capsule based and require a user to insert at least one capsule into the device for each delivery. It can be difficult to accurately monitor the way in which a user uses the device when not directly supervised as some users do not accurately track their usage. This can lead to poor compliance with a therapeutic regimen which is not apparent to a prescriber so the cause of a symptom persisting is not clear. Dispensers have been proposed to enable a user or third party to review the number of doses taken by a user, but this does not necessarily correspond accurately to the number of correct doses actually taken by the user. For example capsules may be removed from a dispenser, but never put into the inhaler, or put into the inhaler, but the medicament not delivered for some reason.

The present invention provides an inhaler comprising a capsule housing for containing a medicament capsule, an airflow path through which air flows during an airflow event from at least one air inlet to an outlet, the airflow path passing through the capsule housing, a first sensor, a processor and a power source for powering the processor, the capsule housing being defined by at least one wall and configured such that when a capsule is located in the capsule housing and sufficient air flows along the airflow path through the capsule housing, the capsule moves within the capsule housing, the first sensor is arranged on the inhaler so that it is able to detect the movement of the capsule within the capsule housing and generate a first signal indicative of said movement, the processor receiving the first signal from the sensor and using said first signal to determine whether the first signal is indicative of the presence, or absence, of a capsule in the capsule housing during an airflow event and generate a capsule signal indicative thereof.

The inhaler is intended to enable the delivery of medicament from the capsule to an airway, for example the lung, of a patient. The medicament may be a dry powder, a liquid or other suitable formulation and may include one or more active components for treating one or more disease states. The medicament may include one or more non-active components which may be for stabilising, bulking or otherwise changing one or more characteristics of the formulation. The medicament may not include any active component, for example the medicament may be a placebo.

The airflow path includes an inlet for allowing air into the airflow path. The term air should be read to include any suitable gas, for example a gas which may be provided to a patient which may not have an identical composition to air, for example oxygen enriched gas. The outlet from the airflow path may be a mouthpiece or nosepiece through which a user inhales in order to receive the medication from the capsule.

An airflow event is when air flows through the airflow path. This may be caused by a user inhaling through the inhaler, for example inhaling through a mouthpiece, or nosepiece, or it could caused by a pressure source causing air, or other gas, to flow though the airflow path from the inlet to the outlet and into a user. Typically the airflow through the inhaler will be in the range between 15 and 150 liters per minute.

The processor may be electronic, for example it may include one or more analogue or digital integrated circuits, discrete circuits or programmable digital processors. The processor may require a power source, for example a source of electrical power to function. The sensor may be electronic and may also require a source or electrical power to function or it may be a passive sensor.

The signals generated by the sensor and/or processor may be electromagnetic and may be a time variable signal, for example a waveform, or may be an electronic on/off or high/low signal or any other suitable form of signal.

The sensor may be any suitable type of sensor able to generate a signal capable of being processed to provide a determination of whether a capsule is present in the inhaler. For example an optical sensor could be arranged to monitor the capsule housing and a signal from said sensor could be processed to determine if the signal is indicative of capsule movement in the capsule housing. It is expected that a basic algorithm and trial and error could produce a suitable way of processing such a signal.

In one embodiment the inhaler includes a first sensor which is an impact sensor and the first signal is an impact signal. The capsule housing is defined by at least one wall and is configured such that as a capsule moves within the capsule housing the capsule repeatedly impacts on the at least one wall. The impact sensor is arranged on the inhaler so that is able to detect the impacts of the capsule on the capsule housing wall and generate an impact signal indicative of each impact.

The first sensor is arranged on the inhaler so that it is able to detect the movement of the capsule within the capsule housing. It may detect the movement directly, for example an optical sensor viewing the capsule movement. In an alternative embodiment the sensor may detect movement indirectly by sensing a parameter that can e analysed to determine the presence or absence of a characteristic linked with movement of the capsule, for example the impact of the capsule with a wall, or a variation in the air flow pattern as the capsule moves across air inlets or outlets.

The advantage of an impact sensor over, for example an optical sensor, is that no part of the impact sensor needs to be disposed in the airflow path which can simplify the construction of the airflow path and may make it easier to retrofit such a sensor to an existing inhaler design. An optical sensor would need at least one window in the airflow path though which it can 'see' into the capsule housing and generate a signal so that the inhaler can process that signal to detect a capsule therein. The impact sensor may be any suitable sensor, for example a pressure transducer, a microphone, or a piezo element.

In one embodiment the sensor is a microphone arranged in the inhaler at a location where impacts of the capsule on the capsule housing wall can be 'heard', or 'felt', by the sensor. The output from more than one type of sensor may be combined to produce a suitable impact signal. It should also be noted that the capsule could be modified to render it more readily detectable by a sensor, for example the capsule may include a metallic or magnetic part which could be detected by a suitable sensor. In another embodiment the sensor is a piezo element arranged in the inhaler at a location where impacts of the capsule on the capsule housing wall can be 'heard', or 'felt', by the sensor.

The inhaler may further include memory for storing the capsule signal for one or more airflow events for later retrieval. This could be any suitable form of memory and may be erasable or permanent. For example the memory may be electronically readable and/or writeable and/or rewritable and might include flash memory, RAM, EPROM. The memory may also record the first signal, data about the time at which the signal was generated and any other data. The inhaler may include additional sensors which could provide use data to the user of a prescriber and such data could be stored in a memory for later retrieval. The data could be associated with particular airflow events.

The inhaler may further include an output from which the capsule signal and/or the contents of a memory can be accessed by an external device, such as a computer. The output may include a socket into which a communication cable can be inserted. Additionally, or alternatively, the output might include a signal generator for generating and transmitting a wireless signal that can be received by an external receiver. The output may be a wireless transmitter, for example a WiFi™ transmitter.

The processor may analyse the first signal using one or more different algorithms. The processor may analyse the first signal from the sensor using a peak finding algorithm and determine whether the calculated peak frequency is within predetermined limits in order to produce a capsule signal. These limits will be determined based on the typical spinning capsule frequency at the expected flow rates within the inhaler geometry. During an airflow event it has been found that the frequency with which the capsule impacts the wall of the capsule housing is substantially consistent and appropriate limits can therefore be generated. A peak finding algorithm is used to reduce the effects of signal noise on the detection of impact events and the computing complexity is relatively low.

The processor may analyse the impact signal from the sensor using a frequency-domain discriminator algorithm and determine if the ratio of signal strength between two different predetermined frequency ranges is within predetermined limits in order to produce a capsule signal. During an airflow event it has been found that the impact signals differ in particular frequency ranges between signals with a capsule present and those with no capsule present. The comparison of the ratio of signal strength between two different predetermined frequency ranges reduces the effects of signal noise.

The processor may analyse the impact signal from the sensor using a two variable statistical algorithm which calculates two statistical variables to characterise the signal and determines if the calculated statistical measures fall into a predetermined domain on a scatter plot of one variable against the other in order to produce a capsule signal.

By performing statistical analysis to calculate statistical variables to characterise the impact signal it has been found that by some measures of the impact signal differ for signals with a capsule present and those with no capsule present.

Kurtosis is a potentially useful statistical variable for this purpose. On a plot of probability against a particular variable (x), if the variable x is Gaussian, then K=0. If, however, K>0 the tails of the distribution are fatter at the expense of the central peak. Conversely, if K<0 then the distribution has leaner tails and a fatter, broader peak. K is thus a bidirectional measure of non-Gaussianity.

Kurtosis (K) can be used for detecting capsule collision transients because these events tend to push the tails of the sample distribution outwards in an observably predictable manner making the result distinctly non-Gaussian. Breath-noise alone is very Gaussian. However, background noise when the inhaler is not being inhaled through has very low power (and therefore a comparatively low variance ($\sigma^2$)) and can have extremely high kurtosis because even very small transients can have a big proportionate impact on the tails of signals. This gives two types of signal that need distinguishing:

Breath noise, capsule absent, (low K, low to medium $\sigma^2$)
Breath noise, capsule present (medium K, low to high $\sigma^2$)

The peak to mean ratio of either the signal itself, or of the square of the signal, can be used as a non-capsule signal tends to have fewer high peaks (impact events) and therefore a lower ratio of peak to mean.

The calculated variables may be kurtosis and variance, or may be the peak-to-mean ratio of the square, or of the magnitude, of the impact signal and variance.

For all these algorithms, the limits that can be used to classify signal types between 'capsule present' and 'capsule not present' will vary from inhaler type to inhaler type and can be determined using simple trial and error methods. There are likely to be minimal variations for inhalers of the same type and so these limits can be readily calculated for an inhaler type.

The capsule housing may be any suitable shape within which a capsule can move sufficiently to allow a sensor to produce appropriate signals. The capsule housing may allow the capsule to move in one or more of the following ways, back and forth longitudinally, radially or rotationally, either fully rotating or through a limited angular extent The capsule housing may include a portion which is substantially cylindrical in shape with a diameter longer than a capsule to be contained therein and a height greater than the diameter of the capsule, but less than the length of the capsule and the airflow path is arranged to make the capsule spin within the capsule housing. This arrangement enables the capsule to spin about an axis passing substantially through its diameter. The spinning may be in addition to a substantially random wobble created by the airflow about other axes.

The inhaler may include at least one actuator which can be actuated by a user to cause an opening element to open a capsule within the inhaler. The inhaler may further include an actuator sensor for sensing actuation of the actuator and generating an actuation signal. The processor may be arranged to receive the actuation signal. The actuator may be a button coupled to an opening member, for example a piercing element or a cutting blade which are adapted to create an opening in the capsule to permit access to a medication continued therein. There may be two actuators, each with an associated opening element so that two openings can be created in a capsule. The actuator sensors may be push button switches. Each actuator may be associated with an actuator sensor, but this need not be the case. The actuator sensors could be used to 'wake up' the rest of the electronics as the pushing of the buttons should be the cat performed by a user just prior to inhaling through the device.

The processor may be arranged to generate a dose signal indicative of whether a user has followed a correct use sequence for the inhaler. The processor may generate the dose signal based upon the capsule signal and the actuation signal, the order in which those signals were generated and the time between those signals.

In any of these examples, one or more filters may be applied to the signal from the, or each, sensor, prior to one or more of the algorithms being applied thereto. The filters may include one or more of a high pass filter, a low pass filter, a noise reduction filter or any other suitable filter.

The inhaler may be substantially similar to, or substantially the same as, the capsule inhaler described in WO2005/113042.

It should be understood that throughout this specification and in the claims that follow, unless the context requires otherwise, the word "comprise", or variations such as "comprises" or "comprising", implies the inclusion of the stated integer or step, or group of integers or steps.

Figure 7:
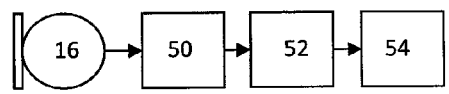
Figure 1:
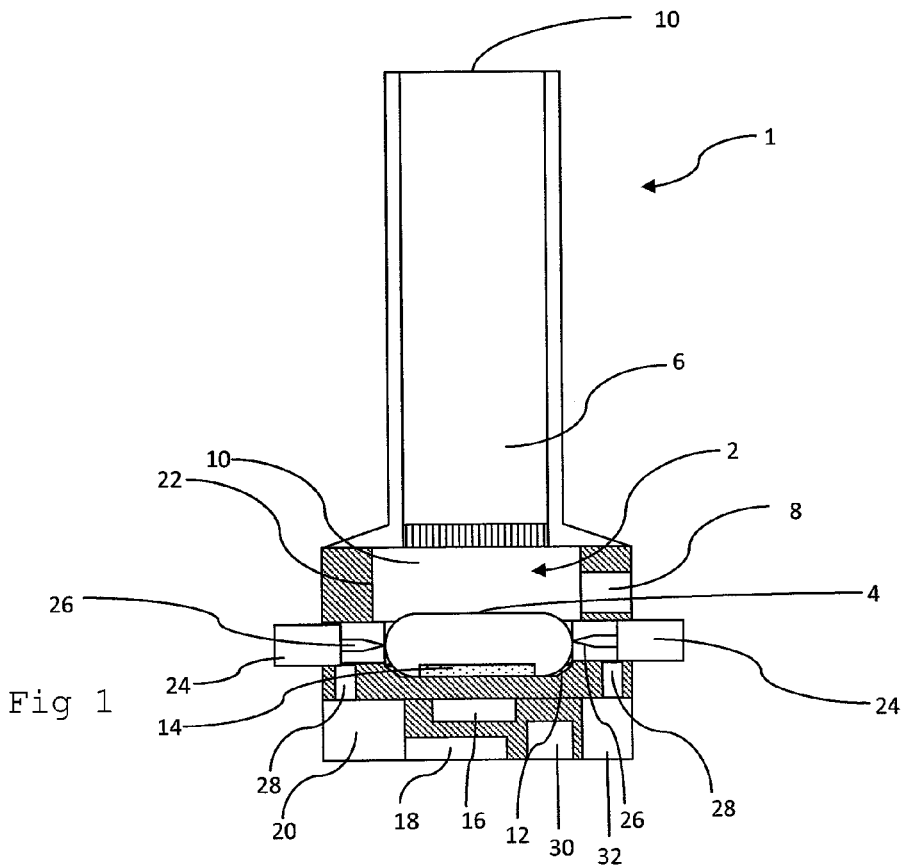
Figure 2:
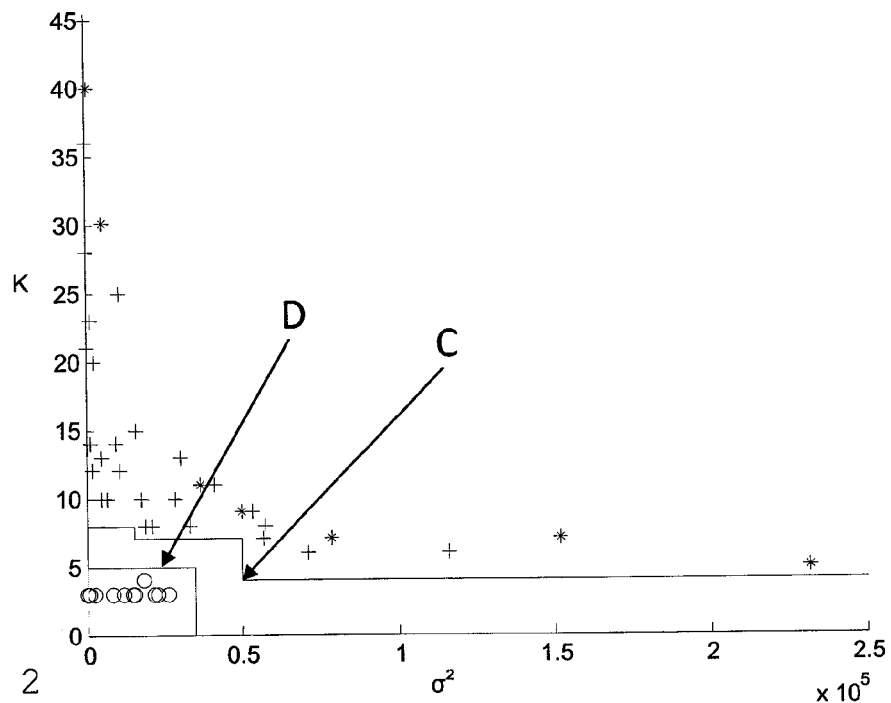
Figure 3:
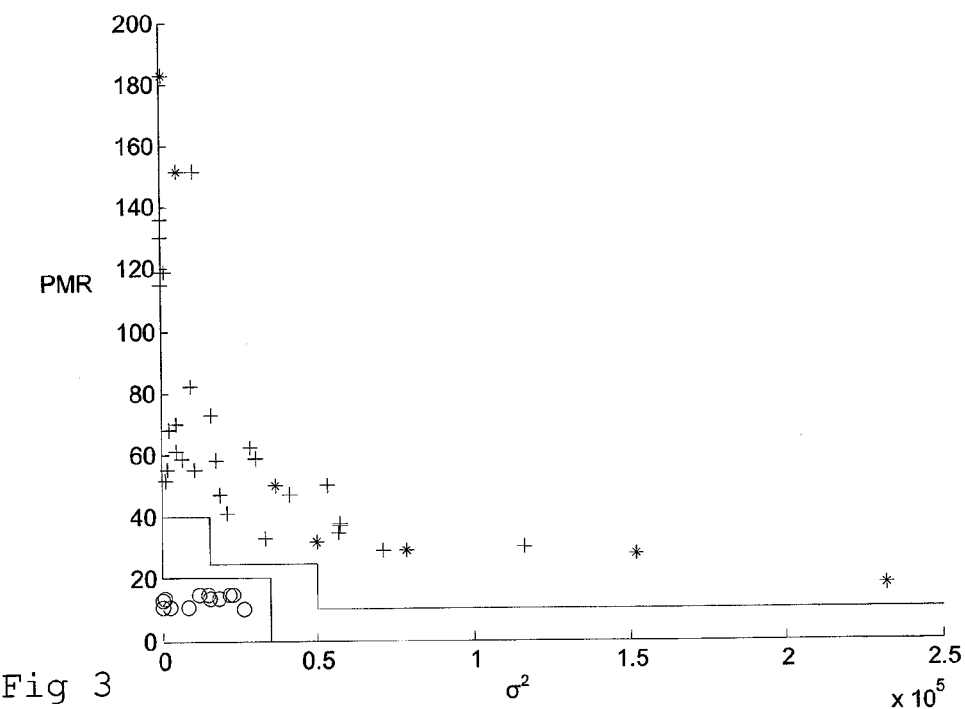
Figure 4:
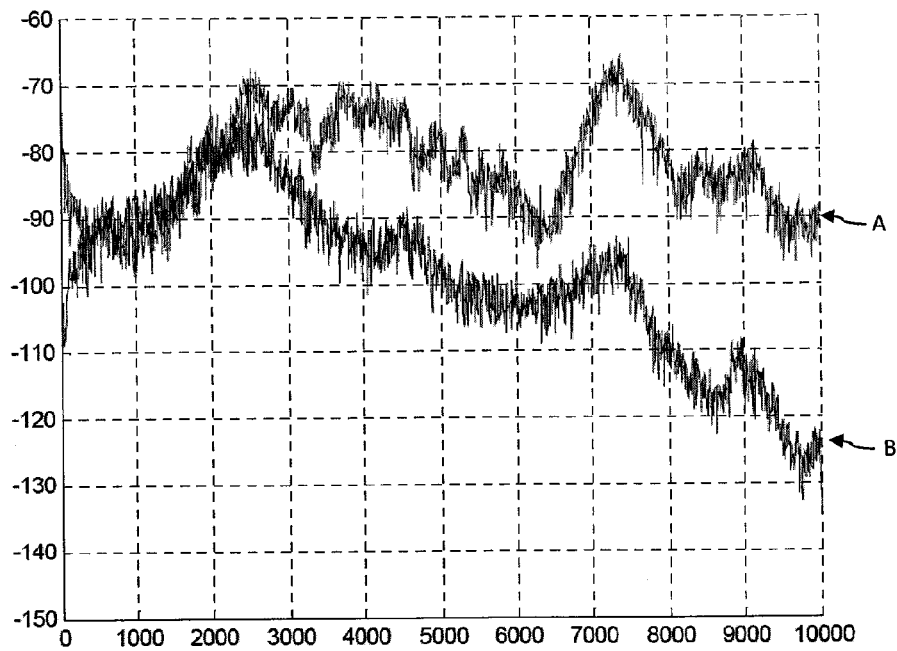
Figure 5A:
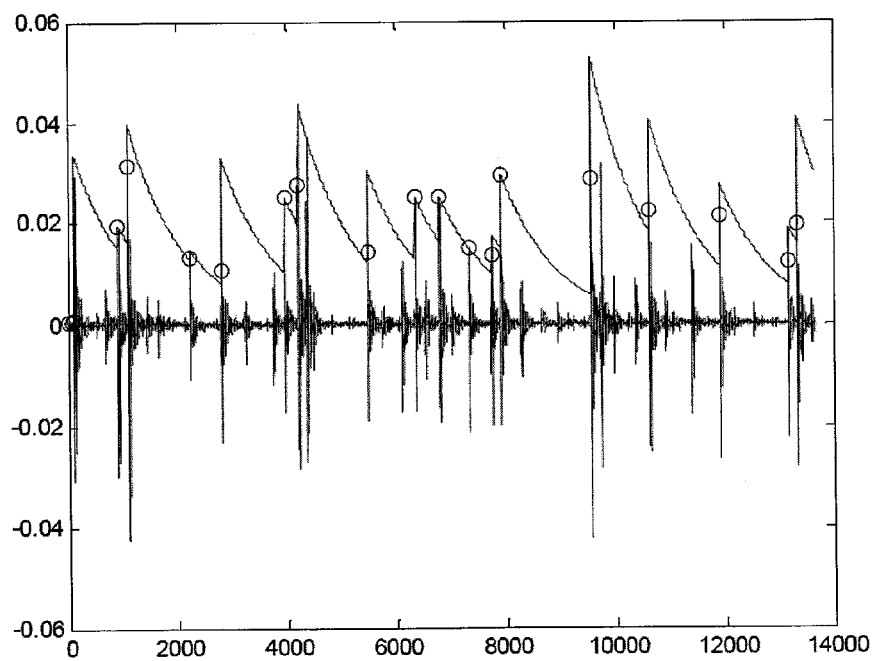
Figure 5B:
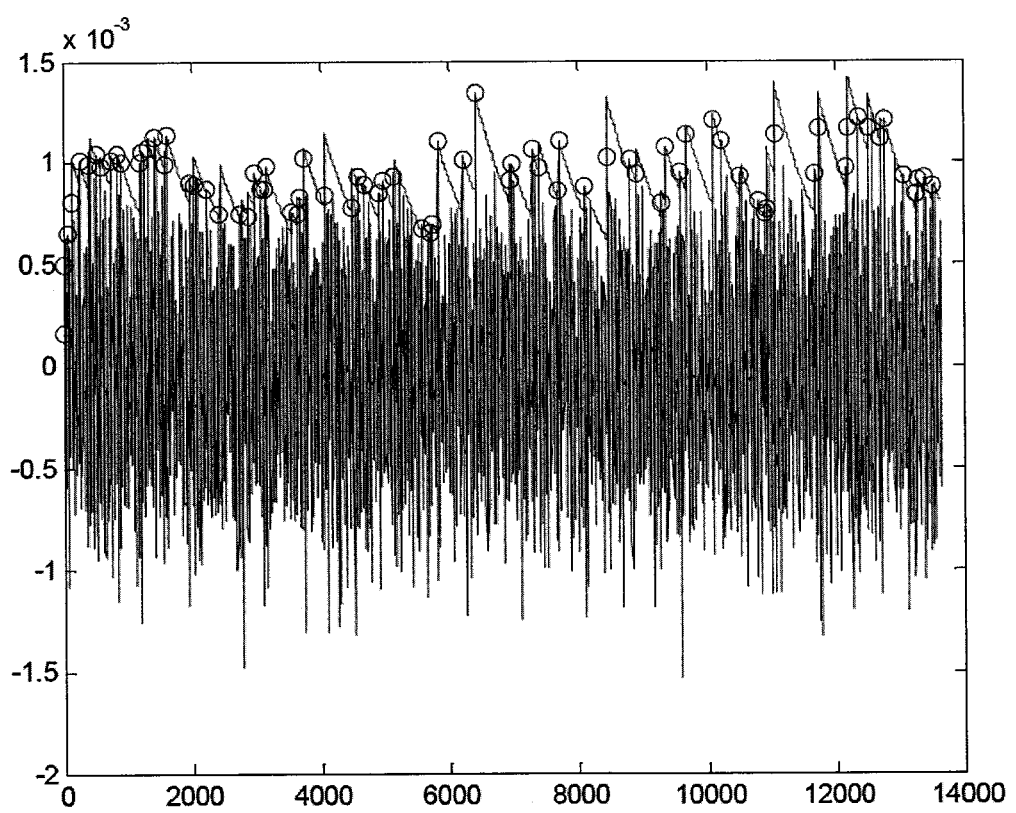

The invention will now be further described, by way of example only, with reference to the following drawings in which:

FIG. 1 shows an inhaler;
FIG. 2 shows a scatter diagram of Kurtosis vs. Variance;
FIG. 3 shows a scatter diagram of Peak-to-Mean Ratio vs. Variance;
FIG. 4 shows a graph of an example of a frequency-domain discriminator analysis;
FIGS. 5a and 5b show a graph showing an example of a peak-hold analysis;
FIG. 6 shows an example of the electronics hardware based on digital processing; and
FIG. 7 shows an example of a signal processing algorithm.

FIG. 1 shows an inhaler 1 comprising a capsule housing 2 containing a medicament capsule 4. The inhaler 1 comprises an airflow path 6 through which air flows during an airflow event. The airflow path 6 extends from at least one air inlet 8 to an outlet 10 and passes through the capsule housing 2. The inlet 8 enters the capsule housing 2 away from a centreline. In this example a top part 10 part of the capsule housing 2 is substantially cylindrical and the air inlet 8 enters substantially tangentially to the capsule housing 2 to encourage the air to swirl within the capsule housing 2. The top part 10 of the capsule housing 2 is substantially cylindrical in shape with a diameter longer than a capsule 4 contained therein and a height greater than the diameter of the capsule, but less than the length of the capsule 4. The capsule housing 2 includes a bottom part 12, or coffin, in which the capsule 4 initially rests. The capsule 4 contains a dry powder medicament formulation 14.

The inhaler 1 further comprises a sensor 16, in this case a microphone, located adjacent the bottom part 12 of the capsule housing 2. The sensor 16 is coupled to a processor 18 which is powered by a power source 20, in this case a battery.

The capsule housing 2 is defined by at least one wall 22 and is configured such that when a capsule 4 is located in the capsule housing 2 and sufficient air flows along the airflow path 6, the capsule 4 is drawn into the top part 10 of the capsule housing 2 and spins in the airflow. As the capsule 4 spins it makes repeated impacts on the wall 22 and the sensor 16 is arranged so that it is able to detect these impacts within the capsule housing 2. The sensor 16 generates a signal indicative of the impacts. The processor 18 receives the signal from the sensor 16.

The inhaler 1 also includes a pair of actuator buttons 24 which are coupled to piercing members 26. The buttons 24 can be pressed by a user to cause the piercing members 26 to pierce holes in the ends of a capsule 4 arranged in the bottom part 12 of the capsule housing 2. There are actuations sensors 28 that can generate actuation signals indicative of whether the actuator button 24 has been pressed or not.

The processor 18 receives the signals from the sensors 16,28 and produces an output signal which may be indicative of one or more of the presence of a capsule during an airflow event, the actuation of the actuation buttons 24, the correct use of the inhaler (correct sequence and timing of the actuation and a capsule being present during an airflow event). The output from the processor 18 and/or the raw output from the sensors are stored in a memory 30 and can be accessed using an output 32, in this case a wireless transmitter.

It should be noted that with a microphone sensor a significant amount of noise may be detected in addition to the detection of the desired impact events. The noise may be environmental, or caused by the airflow through the inhaler. This noise may vary considerably in volume and type so some way to discriminate between a signal indicative of impact and one that does not indicate such impacts is required.

To use the device correctly a user is required to load a capsule into the inhaler, press the buttons to pierce the capsule and then inhale through the device such that the capsule is agitated and spins in the airflow such that a powder medicament therein is dispensed from the capsule and entrained in the airflow to the patient.

The way in which the inhaler electronics might work is a follows:
1. User depresses the buttons and actuation signals received by processor.
2. processor starts sampling data from the first sensor for a predefined period of time. Data are processed on-line according to one or more of the algorithms discussed herein. Intermediate data are stored.
3. Intermediate data are checked for plausibility. Data from multiple approaches are compared if required.
4. Results are stored for later transmission.

Some examples of the way in which the processor may process the impact signal are described below.

A way to detect an impact in the signal from the inhaler when filled with a capsule is to compare the signal with a particular threshold. For example, for low to medium breath flow rates the capsule's impacts can be identified in the signal by applying a threshold and assuming that each exceeding of the threshold was caused by a capsule impact. If during the signal processing a sufficient number of impacts is found, the signal can be determined as indicative of the presence of a capsule. The number of impacts depends on the capsule spinning frequency which depends on the inhaler design and needs calibrating for each inhaler type.

Another method of analysing the signal from the sensor is a statistical approach in which statistical variables are calculated to characterise the signal. A capsule within the inhaler causes a very distinct impact rattle with high signal spikes at a low frequency. This creates a distinctive amplitude distribution in the signal.

For this analysis the signal is first passed through a high pass filter (HPF) with z-transform in equation (1)

$$H(z) = \frac{1 - z^{-1}}{1 - \alpha z^{-1}}, \quad \alpha \in (0, 1) \qquad (1)$$

This has the double effect of (i) reducing low-frequency noise and any DC offset and (ii) boosting high-frequency noise and capsule collision transients.

A sliding window algorithm is then performed operating on N samples of data (typically N=2048), hopping N samples at a time for economy. In each window, the kurtosis K and variance $\sigma^2$ are computed using equations (2) and (3). The sliding window that has maximum power (empirically associated with maximum 'information' over the usage cycle) generates the required $(K, \sigma^2)$ detector output. As the data is assumed to be zero-mean after the HPF, the summations can be performed instantaneously without foreknowledge of the mean.

$$K = \frac{1}{N\sigma^4} \sum_{i=1}^{N} (x_i - \bar{x})^4 - 3 \cong \frac{1}{N\sigma^4} \sum_{i=1}^{N} x_i^4 - 3 \text{ when } \bar{x} \cong 0 \quad (2)$$

$$\sigma^2 = \frac{1}{N} \sum_{i=1}^{N} (x_i - \bar{x})^2 \cong \frac{1}{N\sigma^4} \sum_{i=1}^{N} x_i^2 \text{ when } \bar{x} \cong 0 \quad (3)$$

As described before, Kurtosis is thus a bidirectional measure of non-Gaussianity. If a random variable x is Gaussian, then K=0. If, however, K>0 the tails of the distribution are fatter at the expense of the central peak. Conversely, if K<0 then the distribution has leaner tails and a fatter, broader peak. K Kurtosis is suitable for detecting the capsule impact events because these events tend to push the tails of the sample distribution outwards in an observably predictable manner making the result distinctly non-Gaussian. Breath-noise alone is a lot more Gaussian.

This gives two types of signal that need distinguishing:
Breath noise, capsule absent, (low K, low to medium $\sigma^2$)
Breath noise, capsule present (medium K, low to high $\sigma^2$)

Simulation tests were conducted with the goal of being able to classify an input signal as belonging to one of two classes (H1=breath noise+capsule present, H0=not H1). Some example results are shown in the scatter diagram in FIG. 2.

It shows all data sets recorded using one exemplary microphone type. Two distinct areas of results can be identified in the scatter diagram. Between them is an area where in no results fall. The two areas represent breath noise with a capsule spinning and just breath noise.

As mentioned, environmental noise has a lower Kurtosis. When such a signal is added to the capsule+breath noise signal, the overall Kurtosis becomes smaller. Hence, the data points will move lower in the scatter diagram.

After calculating the variance and Kurtosis, a classification decision on the results must be taken. This is done by checking into which of the three areas delineated by the lines in FIG. 2 the data point falls.

Anything falling above the upper line 'C' represents a signal indicative of a capsule being present. Anything falling below the lower line 'D' represents just breath noise. Anything falling between the two lines represents a capsule with noise.

It is noted that very high levels of environmental noise can mask the capsule noise and hence push the data points from the capsule region into the no capsule region. In order to detect such issues, the techniques described in later can be used.

This algorithm is useful as it is robust, of low computational complexity and has low memory requirements. It is noted that the calculation of Kurtosis requires quite a large dynamic range as squares and squares of squares are to be calculated.

This technique works for sample rates as low as a few kilohertz. Nyquist sampling is not required as long as the peaks can still be sampled.

The previously described higher-order statistical method may be simplified. The goal of that method is to detect the presence of high peaks in the signal while the majority of the signal is quite low. This was done by calculating Kurtosis. A potentially simpler method is to use the peak-to-mean ratio of the square of the signal.

For this method the signal is again passed through the high-pass filter described in equation (1). Then, again variance is calculated for windows of typically 2048 samples. Also, the largest square of a signal sample is recorded for each window. Its value is divided by the mean to become the peak-to-mean ratio.

Variance and peak-to-mean ratio are then used as Variance and Kurtosis before. This is illustrated in FIG. 3.

The same processing as before where the data points are classified according to their area on the scatter plot is performed.

This method has the same low memory requirements as the higher-order statistical method. In addition it requires fewer computations and has a smaller dynamic range. This simplifies operation on cheap and small low-power processors which typically only offer fixed-point computations.

Another algorithm that can be used to analyse the signal from the sensor is a frequency-domain discriminator analysis. FIG. 4 shows a comparison of the analysis of a signal from an airflow event (50 l/min) in the inhaler with a capsule present, Line A, and without, Line B. It is apparent that the frequency spectra with a full capsule and no capsule data are similar in amplitude in the frequency band 1 kHz to 2.5 kHz, but very different at frequencies above 4 kHz which is due to the distinct signals from the impacts of the capsule within the inhaler.

This algorithm compares the signal energy in the 1-2.5 kHz band with that above 3 kHz. This can be carried out by performing a fast Fourier transform and summing the energy in the different bands, or more simply in the time-domain through the use of a combination of band-pass and high-pass filters. These filters and the subsequent energy comparison can be implemented using analogue or digital techniques. This algorithm is useful as there is a low computational complexity, if implemented in time-domain using filters.

From testing at various flowrates and with simulated noise and breath profiles it was found that this method provides a reasonably robust method for detecting the presence of a capsule in the inhaler, even in the presence of high levels of noise. It was noted that the majority of the tested environmental noise's spectral content was below 1000 Hz and so wouldn't affect the energy ratio calculation performed here.

Another method is to apply a peak-detection algorithm, which aims to identify all the peaks in the signal that were cause by the capsule's impacts. Again, the signal is high-pass filtered as in equation (1). The remainder of the algorithm can be performed on the squared samples of the filtered signal or just the filtered signal itself. The signal can be processed in a sliding window-fashion to allow for calculating a profile over time but this is not necessary.

For this algorithm the amplitudes of a samples or its square are compared to a peak-hold value. If the sample is greater than the peak-hold value a new peak-hold event is said to have occurred. In this case the peak counter is incremented and the peak-hold value is set to the sample's value. If, however, the next sample is less in amplitude than the peak-hold value, no peak-hold event is noted, and the current peak-hold value is simply reduced by multiplying it by an appropriate decay factor (in this case a suitable value is about 0.99). The pseudo code for this algorithm is given below where d(k) is kth data sample, and pk_hold is the peak-hold value.

```
IF d(k) > pk_hold
    pk_hold = d(k)
    peak_counter = peak_counter + 1
    peak_event(k) = 1;
ELSE
```

```
pk_hold = 0.999 *pk_hold
END
```

Not shown in the pseudo the code is that in one embodiment of this algorithm at least 20 samples need to have been processed before the next peak-hold event can be deemed to have occurred. This prevents a cluster of peak-hold events occurring around the onset of a capsule impact event and ensures that each impact is counted only once.

Also, low-level noise can be removed using a threshold. Only sample values above a threshold are considered to be valid peaks. This avoids counting many very small peaks that are not actual capsule impacts.

Having found the peak-hold events, the algorithm measures the time between each event from which a fundamental frequency can be calculated. Then the number of occurrences of particular fundamental frequencies within 10 Hz bands are counted. The results of testing with the current inhaler type show that due to well-defined capsule impact events, the impact signal from a full capsule measurement has more low-frequency content than high frequency content, and so comparing the signal energy below 110 Hz to that above 300 Hz this is a suitable metric to differentiate between full capsule and no capsule events.

FIGS. 5a and 5b show the results of peak-hold processing for a full capsule and no capsule measurement respectively. Both tests were conducted at 20 l/min of flow through the inhaler and the graphs show signal amplitude on the vertical axis and the number of samples along the horizontal axis.

The 'o' symbol represents a peak-hold event and the lines joining the 'o's show how it decays between each of these events. It should be noted from the figures that the prominent capsule impact peaks have been located for the full-capsule measurement, but for the no-capsule measurement the algorithm just locates closely spaced peaks due to the nature of noisy waveform.

Tests at higher flowrates (150 l/min) have shown that the individual impact peaks are closer together so there is more high frequency content in the full capsule measurements and as such the ratio between the sub-110 Hz to 300-1000 Hz energy is not as great as that for the lower flow-rate measurements, but is still useable.

While all algorithms described so far provide good performance in ideal, quiet conditions, environmental noise or noise caused by handling the inhaler can cause spurious results.

In order to avoid false results, the following techniques can be used:

Handling noise can cause individual high peaks in the signal. These are quite similar to the peaks caused by capsule impacts. However, only a very limited number of peaks is caused by e.g. dropping the inhaler onto or knocking it against a hard surface. While the statistical algorithms or frequency-domain discriminator can not distinguish such events from capsule events they can be supplemented by the peak-hold method. A capsule present classification for a signal may only be deemed valid if there is a sufficient number of peaks present in a time window. Otherwise the result is classified as noise.

Loud background noises can disguise the signal peaks which are used for detecting a capsule using the various algorithms. As a breath only lasts a limited time there is a time before and after the breath where no capsule and breath noise are to be expected. Hence, the first part of the signal after the buttons are depressed (typically 0.1 to 0.5 seconds after button depress) and the last part before stopping to evaluate the signal (typically after 10 to 30 seconds) can be used for checking the background environmental noise levels. If these are above a certain level which renders the employed capsule detection algorithm(s) unreliable, a noise result shall be created.

FIG. 6 shows the hardware used in the example. The signal from the microphone 16 is passed to an analogue high-pass filter 50 which is a simple 1st order RC filter with a 3 dB frequency of 1 kHz. From there the signal passes to an analogue-to-digital converter (ADC) 52 which samples at 9.6 kHz and has a resolution of 12 bits. The ADC may be integrated into a microprocessor chip 54.

FIG. 7 shows an example of the combination of algorithms that can be performed on the samples once they are sent to the microprocessor 54. First, the signal is sectioned into windows of length 2048 samples in a windowing operation 56.

These are processed by a simple high-pass filter 58. The simplest implementation is a subtraction of the previous sample from the current one. This removes any DC offsets that might be present due to circuitry issues in the ADC. In an example signal there may be an inhalation of about two seconds duration at the start of the signal which is followed by a silent period. The search window has to be much longer than a breath as the time taken by the user between piercing the capsule and inhaling is unknown.

The signal is then squared 60 and the mean of the squared samples is calculated 62 over all 2048 samples of the window. This is performed in the top branch of the algorithm diagram in FIG. 7. Also, the highest square value is recorded 64 in the centre branch. This can be done while computing the squares or via a search over all squared samples if they are stored in memory. After computing all sample squares and their mean and finding their peak-value, the peak-to-mean ratio is computed 66. Both mean of squares (variance) and peak-to-mean ratio are stored for this window for later classification.

The lower branch in the algorithm diagram in FIG. 7 counts the peaks within the window 68. First, a threshold is used to remove small peaks caused by noise. Then the peak detection algorithm is applied to find the peaks caused by the capsule impacts.

This process is repeated for each window until all windows are processed. It is expected that there will be a cluster of results at about zero variance and with a low peak-to-mean ratio. These are the results from the windows which include just environmental noise, for example after the inhalation. Windows during the inhalation tend to produce results with a higher variance and peak to mean ratio.

The classification 70 starts with searching for the window with the highest variance. As this contains the most signal energy, this gives the most reliable information in the presence of other noises. Other measures like searching for a continuous set of windows with highest energy are possible as well to achieve optimum reliability. For the window with the highest variance, the belonging peak-to-mean ratio is looked up in the results.

The result now needs to be classified by comparing it to a set of thresholds. These thresholds were determined by running a large number of experiments with and without capsule for various flow rates. A scatter plot of these experiments' results can typically be divided into four regions:

1. "Capsule" is typically at the top. This is the region of high peak-to-mean ratio (PMR) due to the spikes from the capsule.
2. "Silence". This region has a very low variance and low PMR.
3. "No Capsule". This region has low variance and low PMR. The maximum variance is much lower than the one reached for capsules since no capsule impacts can increase the noise level.
4. "Capsule with Noise". This region falls in between "Capsule" and "No Capsule". Results fall into this region if a capsule signal has been subjected to high levels of environmental noise. As environmental level noise has a lower PMR than capsule noise, it reduces the overall PMR.

Finally, checks against two issues that can arise from the processing done so far are performed. Noises from handling the inhaler 72, e.g. accidentally dropping it onto a hard surface cause large spikes in the signal. These can dominate the variance and cause a very high PMR. This would lead to an erroneous classification as "Capsule". Such handling noise events show typically shown only two to 4 peaks per window while a spinning capsule shows more than 10. Also, due to the duration of a breath, the capsule spins for at least one second. Hence, the number of peaks in five consecutive windows is summed. If this sum is larger than 50, the "Capsule" classification is confirmed. Otherwise, the classification verdict is revised to "Noise".

In some cases a quiet capsule signal can be masked by loud environmental noise. Due to the low PMR this would fall into the "No Capsule" region. To recognise this situation, the variance in the last processed window is checked 74. If it is larger than about twice the silence threshold, the classification verdict is changed to "Noise". This helps to ensure that no, or very few, false negative results are reported.

It should be understood that the invention has been described above by way of example only and that modifications in detail can be made without departing from the scope of the claims.

The invention claimed is:

1. An inhaler comprising:
a medicament capsule housing for containing a medicament capsule,
an airflow path through which air flows during an airflow event from at least one air inlet to an outlet, the airflow path passing through the capsule housing,
a first sensor comprising a microphone or piezo element for detecting impact,
a processor, and
a power source for powering the processor,
the medicament capsule housing being defined by at least one wall and configured such that when the medicament capsule is located in the medicament capsule housing and air flows along the airflow path through the medicament capsule housing, the medicament capsule moves within the medicament capsule housing wherein said movement comprises impacting said at least one wall, the first sensor is being arranged on the inhaler so that it is able to detect the impact of the medicament capsule against said wall of the medicament capsule housing and generate a first signal indicative of said movement, the processor receiving the first signal from the first sensor and analyzes said first signal using a peak-detection algorithm which determines whether the calculated peak frequency is within predetermined limits to determine whether the first signal is indicative of the a presence, or absence, of the medicament capsule in the medicament capsule housing during as the airflow event and to generate a signal indicative of medicament capsule presence,
the inhaler further comprising memory for storing the signal indicative of medicament capsule presence or absence, and an output from which the medicament capsule presence or absence signal or the contents of the memory can be accessed, and at least one actuator which can be actuated by a user to cause an opening element to open the medicament capsule within the inhaler, the inhaler further including an actuator sensor for sensing actuation of the actuator and generating an actuation signal, the processor being arranged to receive the actuation signal.

2. An inhaler comprising:
a medicament capsule housing for containing a medicament capsule,
an airflow path through which air flows during an airflow event from at least one air inlet to an outlet, the airflow path passing through the medicament capsule housing,
a first sensor comprising an impact sensor,
a processor, and
a power source for powering the processor,
the medicament capsule housing being defined by at least one wall and configured such that when the medicament capsule is located in the medicament capsule housing and air flows along the airflow path through the medicament capsule housing, the medicament capsule moves within the medicament capsule housing wherein said movement comprises impacting said at least one wall, the first sensor being arranged on the inhaler so that it is able to detect the impact of the medicament capsule against said wall of the medicament capsule housing and generate a first signal indicative of said movement, the processor receiving the first signal from the first sensor and analyzing the impact signal from the sensor using a frequency-domain discriminator algorithm to determine if a ratio of signal strength between two different predetermined frequency ranges is within predetermined limits in order to generate a signal indicative of medicament capsule presence.

3. An inhaler, comprising:
a medicament capsule housing for containing a medicament capsule,
an airflow path through which air flows during an airflow event from at least one air inlet to an outlet, the airflow path passing through the medicament capsule housing,
a first sensor comprising an impact sensor,
a processor, and
a power source for powering the processor,
the medicament capsule housing being defined by at least one wall and configured such that when the medicament capsule is located in the capsule housing and air flows along the airflow path through the medicament capsule housing, the medicament capsule moves within the medicament capsule housing wherein said movement comprises impacting said at least one wall, the first sensor being arranged on the inhaler so that it is able to detect the impact of the medicament capsule against said wall of the medicament capsule housing and generate a first signal indicative of said movement, the processor receiving the first signal from the first sensor and analyzing the impact signal from the first sensor using a two variable statistical algorithm which calculates two statistical variables to characterize the first signal and determines if the calculated statistical variables fall into a predetermined domain on a scatter plot of one variable against the other in order to produce a signal indicative of medicament capsule presence or absence.

4. The inhaler as claimed in claim 3, in which the calculated statistical variables are kurtosis and variance.

5. The inhaler as claimed in claim 3, in which the calculated statistical variables comprise variance, and a peak-to-mean ratio of the square of the impact signal, or a peak-to-mean ratio of the magnitude of the impact signal.

6. The inhaler as claimed in claim 1, in which the processor analyses the impact signal from the sensor using at least two different algorithms.

7. The inhaler as claimed in claim 3, in which the first sensor comprises a microphone or a piezo element.

8. The inhaler as claimed in claim 1, in which the medicament capsule housing includes a portion which is substantially cylindrical in shape with a diameter longer than a medicament capsule to be contained therein and a height greater than a diameter of the medicament capsule, but less than a length of the medicament capsule and wherein the airflow path is arranged to make the medicament capsule spin within the medicament capsule housing.

9. The inhaler as claimed in claim 3, in which the inhaler includes at least one actuator which can be actuated by a user to cause an opening element to open the medicament capsule within the inhaler, the inhaler further including an actuator sensor for sensing actuation of the actuator and generating an actuation signal, the processor being arranged to receive the actuation signal.

10. The inhaler as claimed in claim 9, in which the processor is arranged to generate a dose signal indicative of whether the user has followed a correct use sequence for the inhaler, the processor generating the dose signal based upon the medicament capsule presence signal and the actuation signal, the order in which those signals were generated and a time between signals.

* * * * *